US008932285B2

(12) United States Patent
Morris et al.

(10) Patent No.: US 8,932,285 B2
(45) Date of Patent: Jan. 13, 2015

(54) ELECTROSURGICAL INSTRUMENT WITH LONGITUDINAL AND LATERAL ACTION

(75) Inventors: David W. Morris, Rhondda (GB); Robert C. Humble, Monmouthshire (GB); Robert J. Brewer, Newport (GB)

(73) Assignee: Gyrus Medical Limited, Cardiff (GB)

( * ) Notice: Subject to any disclaimer, the term of this patent is extended or adjusted under 35 U.S.C. 154(b) by 957 days.

(21) Appl. No.: 13/016,318

(22) Filed: Jan. 28, 2011

(65) Prior Publication Data

US 2011/0196364 A1    Aug. 11, 2011

Related U.S. Application Data

(60) Provisional application No. 61/282,380, filed on Feb. 1, 2010.

(30) Foreign Application Priority Data

Feb. 1, 2010    (GB) .................................. 1001641.8

(51) Int. Cl.
*A61B 18/14*    (2006.01)
*A61B 17/00*    (2006.01)
(Continued)

(52) U.S. Cl.
CPC ..... *A61B 18/1402* (2013.01); *A61B 2017/0088* (2013.01); *A61B 2018/00589* (2013.01);
(Continued)

(58) Field of Classification Search
USPC ............................................... 606/27, 34, 41
See application file for complete search history.

(56) References Cited

U.S. PATENT DOCUMENTS 5,697,909 A    12/1997    Eggers et al.

6,004,319 A    12/1999    Goble et al.
(Continued)

FOREIGN PATENT DOCUMENTS

EP    2 047 816    4/2009
JP    9-501328    11/1994
(Continued)

OTHER PUBLICATIONS

International Search Report issued in Application No. PCT/GB2011/000099, Date of Mailing: Apr. 21, 2011.
(Continued)

*Primary Examiner* — Michael Peffley
*Assistant Examiner* — Daniel Fowler
(74) *Attorney, Agent, or Firm* — Nixon & Vanderhye PC

(57) ABSTRACT

An electrosurgical instrument is provided for the treatment of tissue, the instrument comprising an instrument shaft (10) having a longitudinal axis, and an electrode assembly at one end of the shaft. The electrode assembly comprises a first tissue treatment electrode (11), a second tissue treatment electrode (14), and a third electrode (25) which is electrically insulated from the first and second tissue treatment electrodes by means of an insulation member (12). The first and second tissue treatment electrodes (11, 14) each have an exposed surface for treating tissue, the exposed surface of the first tissue treatment electrode (11) being such as to treat tissue disposed on the longitudinal axis, and the exposed surface of the second tissue treatment electrode (14) being such as to treat tissue disposed laterally of the longitudinal axis. The instrument has a first set of connections (62A, 62B) by which the first tissue treatment electrode (11) can be placed in circuit with the second electrode (14) such that, in use, a current path is established therebetween. The instrument has a second set of connections (62B, 62C) by which the second tissue treatment electrode (14) can be placed in circuit with the third electrode (25) such that, in use, a current path is established therebetween.

15 Claims, 5 Drawing Sheets

Figure 1:
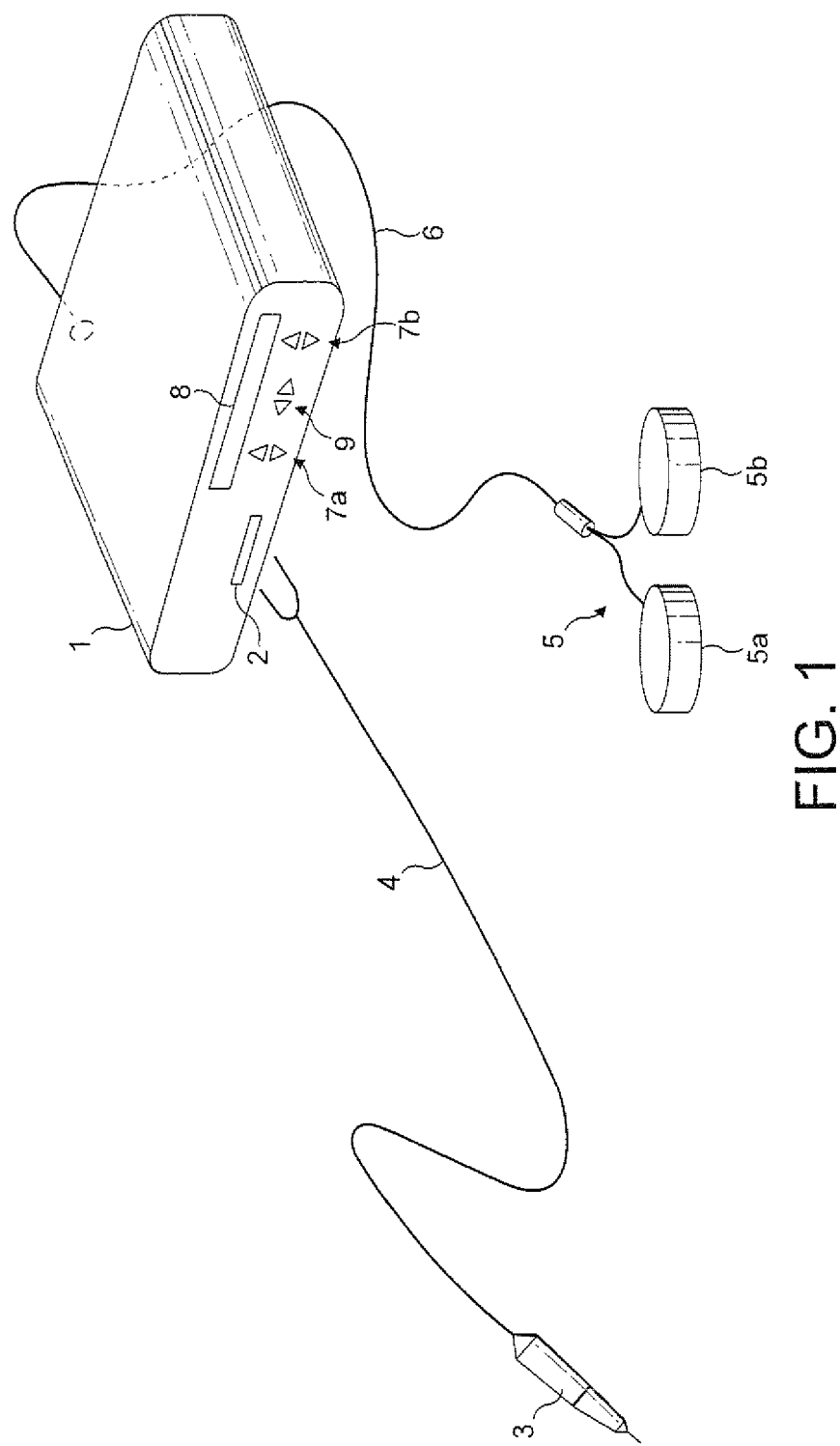

(51) Int. Cl.
*A61B 18/00* (2006.01)
*A61B 18/16* (2006.01)

(52) U.S. Cl.
CPC ............... *A61B2018/00922* (2013.01); *A61B 2018/1467* (2013.01); *A61B 2018/1472* (2013.01); *A61B 2018/162* (2013.01); *A61B 2218/002* (2013.01); *A61B 2218/008* (2013.01)
USPC .......................................................... 606/41

(56) References Cited

U.S. PATENT DOCUMENTS

| | | | |
|---|---|---|---|
| 6,293,942 | B1 | 9/2001 | Goble et al. |
| 6,413,256 | B1* | 7/2002 | Truckai et al. ................. 606/41 |
| 6,832,998 | B2 | 12/2004 | Goble |
| 6,966,907 | B2 | 11/2005 | Goble |
| 7,214,224 | B2* | 5/2007 | Goble ............................. 606/34 |
| 7,241,293 | B2* | 7/2007 | Davison .......................... 606/41 |
| 2002/0049438 | A1* | 4/2002 | Sharkey et al. ................. 606/41 |
| 2004/0153057 | A1* | 8/2004 | Davison .......................... 606/41 |
| 2005/0080409 | A1* | 4/2005 | Young et al. .................... 606/41 |
| 2007/0078457 | A1* | 4/2007 | Paul et al. ....................... 606/50 |
| 2008/0234673 | A1 | 9/2008 | Marion et al. |
| 2009/0093804 | A1 | 4/2009 | Newton |
| 2010/0152726 | A1 | 6/2010 | Cadouri et al. |

FOREIGN PATENT DOCUMENTS

| | | |
|---|---|---|
| WO | WO 94/26228 | 11/1994 |
| WO | WO 00/71043 | 11/2000 |
| WO | WO 2007/092101 | 8/2007 |

OTHER PUBLICATIONS

Written Opinion issued in Application No. PCT/GB2011/000099, Date of Mailing: Apr. 21, 2011.
Search Report issued in Priority Application No. GB1001641.8, Date of Search: May 24, 2010.
Japanese Office Action Patent Application No. 2012-550507 dated Oct. 7, 2014.
English translation of Japanese Office Action for corresponding Japanese Application No. 2012-550507; dated Oct. 7, 2014.

* cited by examiner

ELECTROSURGICAL INSTRUMENT WITH LONGITUDINAL AND LATERAL ACTION

This application claims priority to United Kingdom Application No. 1001641.8, filed 1 Feb. 2010 and claims the benefit of U.S. Provisional Application No. 61/282,380, filed 1 Feb. 2010, the entire contents of which are hereby incorporated by reference.

This invention relates to an electrosurgical instrument for the treatment of tissue. Such systems are commonly used for the vaporisation and/or coagulation of tissue in surgical intervention, most commonly in "keyhole" or minimally invasive surgery, but also in "open" surgery.

It is often the case that, during a surgical procedure, the surgeon is required to remove a first instrument and insert a second instrument, in order to achieve a particular tissue effect. The present invention attempts to provide an electrosurgical system having a surgical instrument that can be used in more than one manner, so as to reduce the number of times that an alternative instrument needs to be used.

Accordingly, an electrosurgical instrument is provided for the treatment of tissue, the instrument comprising an instrument shaft having a longitudinal axis, and an electrode assembly at one end of the shaft, the electrode assembly comprising first, second and third electrodes which are electrically insulated one from another by means of one or more insulation members, the first and second electrodes each having an exposed surface for treating tissue, the exposed surface of the first electrode being such as to treat tissue disposed on the longitudinal axis, and the exposed surface of the second electrode being such as to treat tissue disposed laterally of the longitudinal axis, the instrument having a first set of connections by which the first electrode can be placed in circuit with the second electrode such that, in use, a current path is established between the first and second electrodes, and a second set of connections by which the second electrode can be placed in circuit with the third electrode such that, in use, a current path is established between the second and third electrodes, the arrangement being such that the second electrode acts as an active electrode when the instrument is operated to treat tissue disposed laterally of the longitudinal axis, and as a return electrode when the instrument is operated to treat tissue disposed in the longitudinal axis.

By providing an electrosurgical instrument that can treat tissue disposed on the longitudinal axis (an "end-effect instrument"), as well as treating tissue laterally of said longitudinal axis (a "side-effect instrument") the present invention allows a surgeon to perform different surgical actions with the same instrument, as opposed to withdrawing a first instrument and inserting a second. By using the first electrode, the surgeon has an end-effect instrument, while using the second electrode provides the user with a side-effect instrument. The user can switch between these two modes of operation without needing to withdraw the instrument from the surgical site.

The second electrode is designed to act as an active electrode when the instrument is operated to treat tissue disposed laterally of the longitudinal axis, and as a return electrode when the instrument is operated to treat tissue disposed on the longitudinal axis.

According to one convenient arrangement, the second electrode comprises first and second portions in electrical connection one with the other. The first portion of the second electrode acts as the active electrode when the instrument is operated to treat tissue disposed laterally of the longitudinal axis, while the second portion of the second electrode acts as the return electrode when the instrument is operated to treat tissue disposed in the longitudinal axis. The first portion of the second electrode is preferably substantially planar, while the second portion of the second electrode is conveniently in the form of a ring circumnavigating the shaft of the instrument. The first and second portions of the second electrode are preferably integrally formed from a single metallic component.

According to a preferred arrangement, the second electrode is set back axially with respect to the first electrode. This is conveniently achieved by positioning the first electrode on the extreme distal end of the instrument. Conveniently, the third electrode is also set back axially with respect to the first and second electrodes, and the third electrode is typically is in the form of a metallic sheath provided on the instrument shaft.

In order to provide aspiration of vaporised tissue, a suction lumen is preferably provided, extending along the length of the shaft. The first electrode is conveniently provided with at least one aperture in communication with the suction lumen, to allow tissue vaporised by the first electrode to be aspirated via the suction lumen. Conceivably, the lumen could additionally or alternatively be used for the supply of fluid to the distal end of the instrument.

The invention also extends to an electrosurgical system including a generator for generating radio frequency power, and an electrosurgical instrument, the generator comprising;
 (i) a radio frequency output stage having at least a pair of radio frequency output lines,
 (ii) a power supply coupled to the output stage for supplying power to the output stage,
 (iii) a controller capable of varying a radio frequency signal supplied to the radio frequency output lines;
the electrosurgical instrument comprising an instrument shaft having a longitudinal axis, and an electrode assembly at one end of the shaft, the electrode assembly comprising first, second and third electrodes which are electrically insulated one from another by means of one or more insulation members, the first and second electrodes each having an exposed surface for treating tissue, the exposed surface of the first electrode being such as to treat tissue disposed on the longitudinal axis, and the exposed surface of the second electrode being such as to treat tissue disposed laterally of the longitudinal axis,
the system further including a switch means and a switching circuit operable in response to the switch means to vary the connections between the radio frequency output lines and the first, second and third electrodes such that, in a first configuration, the first electrode is placed in circuit with the second electrode such that, in use, a current path is established between the first and second electrodes so as to treat tissue adjacent the first electrode disposed in the longitudinal axis, and, in a second configuration, the second electrode is placed in circuit with the third electrode such that, in use, a current path is established between the second and third electrodes so as to treat tissue adjacent the second electrode disposed laterally of the longitudinal axis.

This electrosurgical system includes the switch means by which the surgeon can select either the end-effect mode or the side effect mode of operation. Conveniently, the switch means comprises a footswitch, although as an alternative the switch means conceivably comprises a handswitch carried on the electrosurgical instrument. Alternatively, the switch means can be located on the generator. The switch means activates the switching circuit, which is conveniently a part of the generator, although as an alternative the switching circuit is conceivably a part of the electrosurgical instrument.

In a first arrangement, the generator and electrosurgical instrument are such that the instrument is designed to be operated in a conductive fluid, with the conductive fluid completing the current path between the electrodes. This means that the system operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage setting used by the generator are such that the conductive fluid surrounding the electrodes is vaporised when the electrosurgical instrument is operated in its cutting mode.

Alternatively, the generator and electrosurgical instrument are such that the instrument is designed to be operated in a dry-field environment, with the electrodes being in direct contact with the tissue to be treated, and with the tissue completing the current path therebetween. An example of this type of electrosurgical system is given in our earlier U.S. Pat. No. 6,832,998. The power and voltage settings used by the generator are generally lower than in underwater electrosurgical systems, as the electrodes contact the tissue directly and there is no need to form a pocket of vaporised saline surrounding the electrode.

Figure 2:
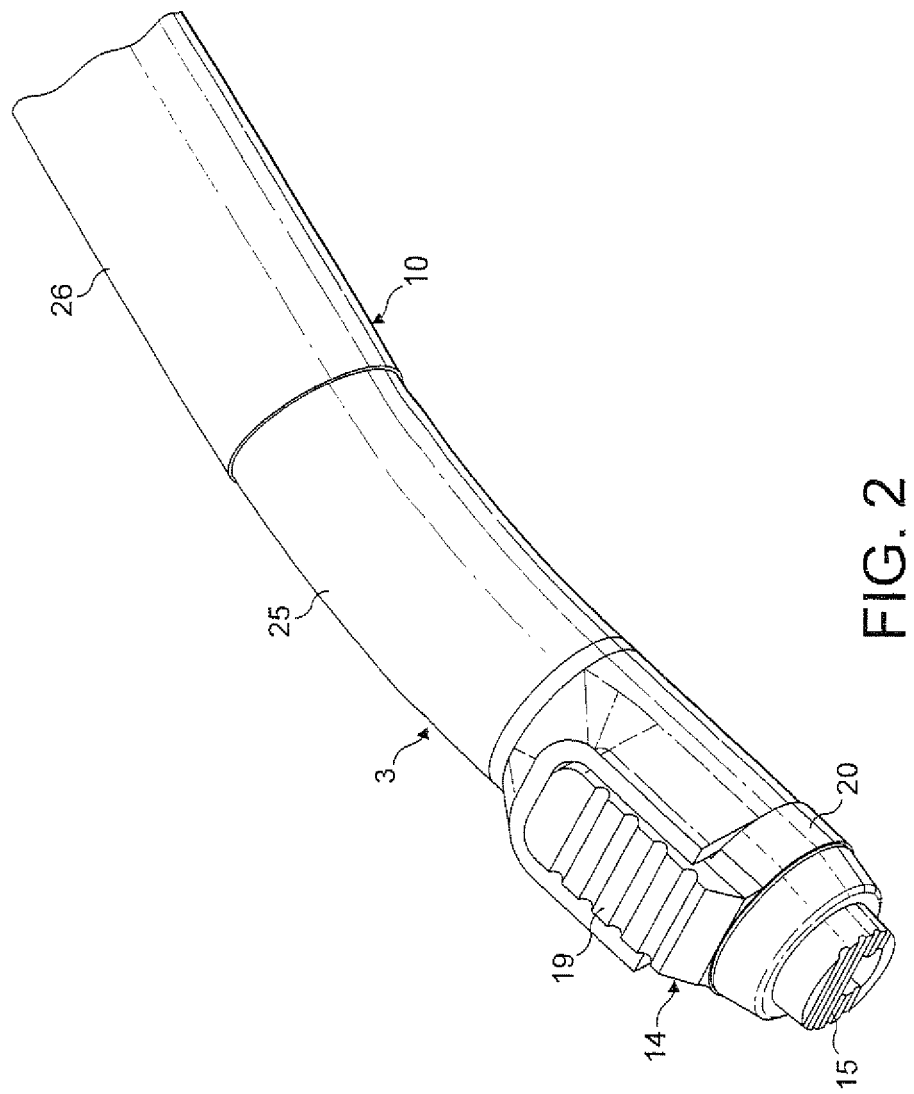
Figure 3:
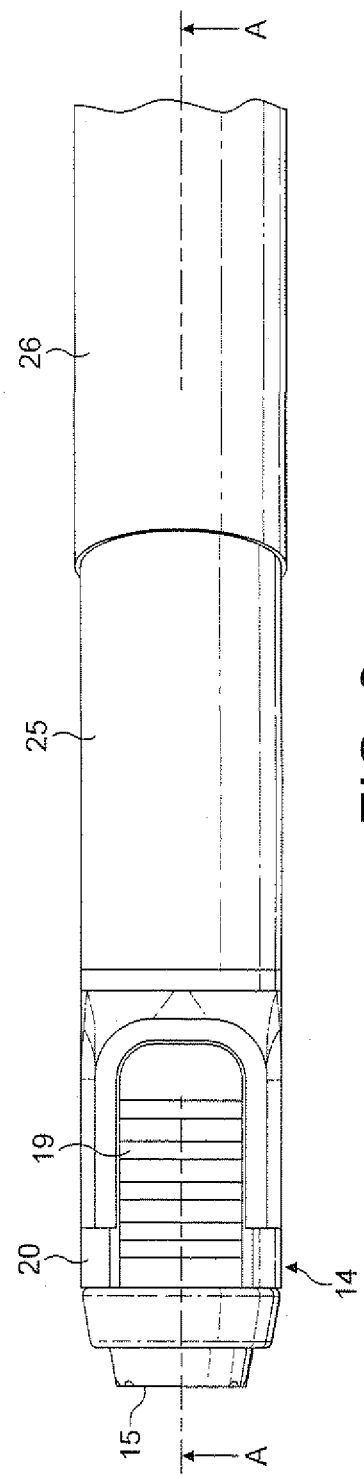
Figure 4:
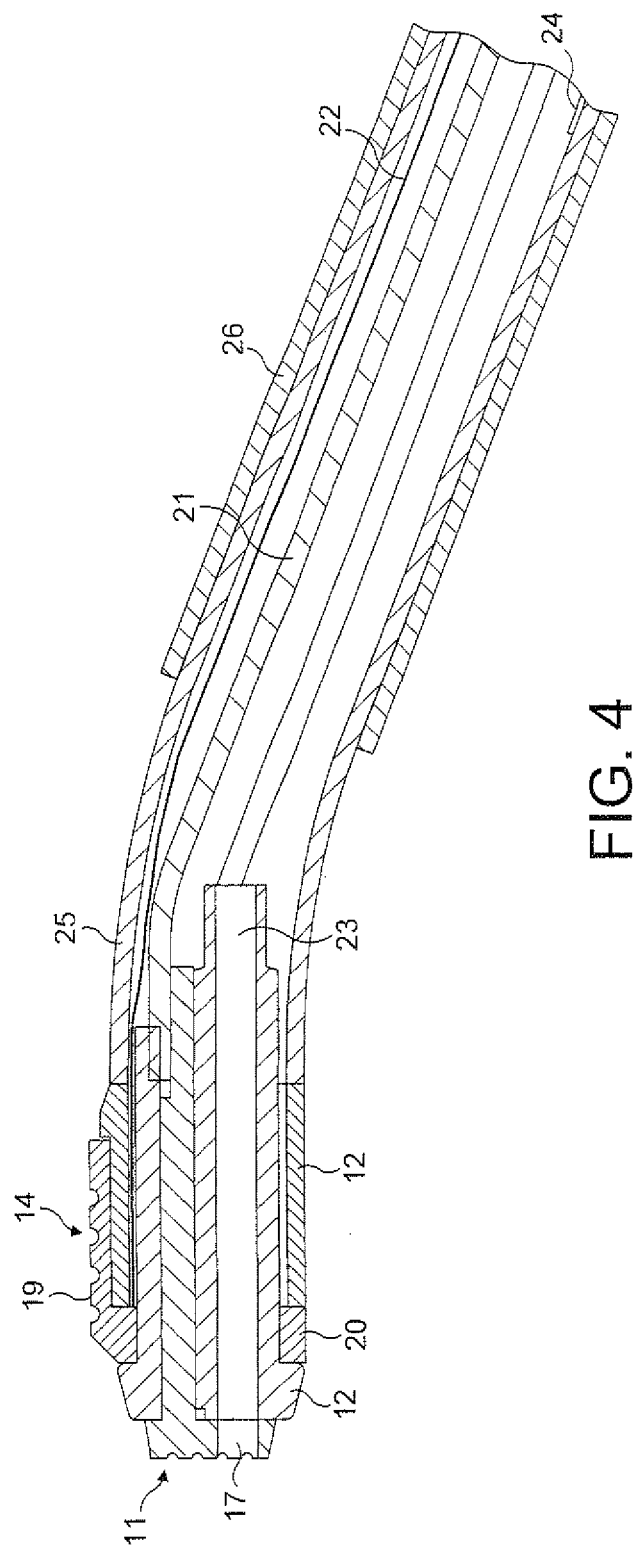
Figure 5A:
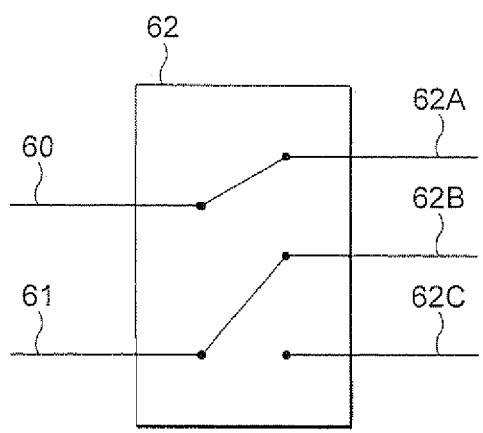
Figure 5B:
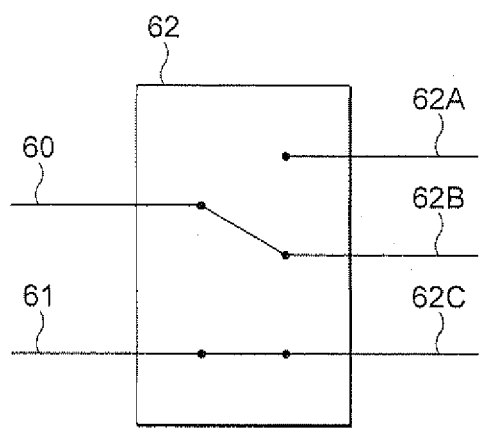

The invention will now be further described, by way of example only, with reference to the drawings, in which:

FIG. 1 is a schematic diagram of an electrosurgical system constructed in accordance with the present invention, FIG. 2 is a perspective view of an electrosurgical instrument constructed in accordance with the present invention, and capable of being used in the system of FIG. 1, FIG. 3 is a plan view of the electrosurgical instrument of FIG. 2, FIG. 4 is a cross-section view of the electrosurgical instrument of FIG. 3, taken along the line A-A, and FIGS. 5A and 5B are schematic block diagrams of the output stage of the electrosurgical generator of FIG. 1, shown in different stages of operation.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 comprises a shaft 10 with electrodes at its distal end, as will be described below. FIGS. 2 to 4 show a first electrode 11 located in a ceramic insulator 12, this electrode comprising a circular end face 15, and a flat portion 18 which serves to locate the electrode within the insulator 12. The end face 15 provides a tissue treatment surface for the first electrode 11. A second electrode 14 is also mounted on the insulator 12, the electrode 14 being mounted on the lateral side face of the insulator 12. Both the electrodes 11 and 14 are formed of tungsten or an alloy of tungsten and platinum.

The first electrode 11 is provided with a suction aperture 17, which is in communication with a suction lumen 23 extending along the shaft 10. In order to reduce the problems of vapour bubble production, and to assist with the removal of particulate material (such as tissue debris) from the region surrounding the electrode 11, the suction lumen 23 is connected to a suction pump (not shown) which can remove vapour bubbles via the shaft of the instrument through the aperture 17.

The second electrode 14 comprises first and second portions 19 and 20, the first portion being a planar portion providing a tissue treatment surface for the second electrode 14. The second portion is a ring 20, which extends around the shaft 10 overlapping the ceramic insulator 12. The ring 20 is located at the distal end of the planar portion 19, and extends completely around the shaft 10 in correspondence with the circular end face 15. In this way, the separation between the end face 15 and the ring 20 is similar at all angular locations around the shaft. A third electrode 25 is provided by the distal end portion of the shaft 10, and a polytetrafluoroethylene, a polyolefin, a polyester or ethylene tetrafluoroethylene sleeve 26 surrounds the proximal portion of the shaft 10 adjacent to the electrode 25. Leads 21, 22 and 24 connect the electrodes 11, 14 and 25 to the RF generator 1 shown in FIG. 1.

The RF generator 1 delivers an electrosurgical current to the instrument 3. The generator 1 includes means for varying the delivered output power to suit different electrosurgical requirements, such as vaporisation or coagulation. The generator 1 is typically as described in our earlier U.S. Pat. No. 6,293,942, with a switching circuit 62 (see FIGS. 5A and 5B) for switching the output lines from the generator to the electrosurgical instrument 3.

The switching circuit 62 comprises connections 60 and 61 from the generator 1, and output connections 62A, 62B and 62C respectively. The output connection 62A is connected to the first electrode 11 via the lead 21, while the output connection 62B is connected to the second electrode 14 via the lead 22. Similarly, the output connection 62C is connected to the third electrode 25, via the lead 24. The operation of the electrosurgical system will now be described.

When the user of the system wishes to use the instrument 3 as an end-effect instrument, the user sends signals (via the footswitch unit 5 or via the push buttons 9 on the generator 1) to set the switching circuit 62 into the condition shown in FIG. 5A. In this condition, the connections 60 and 61 from the generator 1 are connected to the output connections 62A and 62B, and hence to the first electrode 11 and the second electrode 14 respectively. RF power from the generator 1 is supplied to the electrodes 11 and 14, and hence tissue can be vaporised or coagulated as desired at the end of the shaft 10. The end face 15 of the first electrode 11 acts as the active tissue treatment portion, and the ring 20 of the second electrode 14 acts as a return electrode. As mentioned previously, the separation between the end face 15 and the ring 20 is similar at all angular locations around the shaft 10, ensuring an even current density between the two electrodes 11 and 14 when in use.

Alternatively, when the user of the system wishes to use the instrument 3 as a side-effect instrument, the user sends signals to set the switching circuit 62 into the condition shown in FIG. 5B. In this condition, the connections 60 and 61 from the generator 1 are connected to the output connections 62B and 62C, and hence to the second electrode 14 and the third electrode 25 respectively. RF power from the generator 1 is supplied to the electrodes 14 and 25, and hence tissue can be vaporised or coagulated as desired laterally of the shaft 10. The planar portion 19 acts as a tissue treatment face, and the forward location of the ring 20 with respect to the planar portion ensures that the ring has only a minimal effect on the current density between the planar portion and the electrode 25 which acts as a return electrode.

In this way, the surgeon can change between using the instrument 3 as either an end-effect instrument or as a side-effect instrument merely by operating the footswitch (or other controls), and without withdrawing the instrument from the surgical site. The versatility provided by this arrangement allows for a single instrument effectively to perform the function of two instruments, as desired.

As described above, both the end-effect electrode 11 and the side-effect electrode 14 are capable of performing both tissue vaporisation and coagulation. Alternatively, the side-effect electrode can be designed primarily for coagulation (hence the electrode 14 is not provided with a suction aperture similar to the suction aperture 17 of the electrode 11). If, however, the electrode 14 is intended to perform tissue vaporisation, it can be provided with a suction aperture like the electrode 11.

The instrument 3 is designed to be operated in a conductive fluid such as saline, with the fluid completing the circuit between the electrodes 11, 14 and 25. However, the instrument 3 can also be used as a dry-field instrument, in which case the user must ensure that the electrodes are placed in contact with the tissue to be treated.

Alternative embodiments will be envisaged by those skilled in the art without departing from the scope of the present invention. For example, the electrosurgical instrument can also be used for delivering a blended power output. This is achieved by automatically alternating the output of the RF generator 1 between the coagulation and vaporisation power levels, so that more haemostasis is produced then is possible in the vaporisation mode. As a consequence, the speed of tissue debulking is reduced, but the increased haemostasis is useful when cutting or debulking vascular tissue structures. In one arrangement, the blended output is supplied to whichever pair of electrodes is selected, i.e. either the end-effect electrodes 11 and 14, or the side-effect electrodes 14 and 25. Alternatively, the blended power output can be delivered to different electrode pairs, as described in our earlier U.S. Pat. No. 6,966,907. In this arrangement, a blend of RF vaporisation and coagulation voltages is provided by the generator, with the RF cutting voltage being supplied to one pair of electrodes (typically the electrodes 11 and 14) and the RF coagulation voltage being supplied to the other pair of electrodes (typically the electrodes 14 and 25). In this way, simultaneous tissue cutting and coagulation is made possible, using bipolar electrode pairs designed specifically for each tissue effect. It will be appreciated that some of these arrangements may require more sophisticated switching circuits than those described with reference to FIGS. 5A and 5B, but that these can be provided by those skilled in the art without undue difficulty.

Alternatively, the output of the RF generator 1 can be pulsed at the vaporisation power level, without cycled activation of the coagulation mode. This produces a less aggressive tissue vaporisation than occurs in the vaporisation mode, with a consequent reduction in both bubble formation and the risk of tissue charring.

The invention claimed is:

1. An electrosurgical instrument for the treatment of tissue, the instrument comprising an instrument shaft having a longitudinal axis, and an electrode assembly at one end of the shaft, the electrode assembly comprising first, second and third electrodes which are electrically insulated one from another by means of one or more insulation members, the first and second electrodes each having an exposed surface for treating tissue, the exposed surface of the first electrode being such as to treat tissue disposed in the longitudinal axis, and the exposed surface of the second electrode being such as to treat tissue disposed laterally of the longitudinal axis, the instrument having a first set of connections by which the first electrode can be placed in circuit with the second electrode such that, in use, a current path is established between the first and second electrodes, and a second set of connections by which the second electrode can be placed in circuit with the third electrode such that, in use, a current path is established between the second and third electrodes, the arrangement being such that the second electrode comprises distinct first and second portions in electrical connection one with the other, the first portion of the second electrode being substantially planar and the second portion of the second electrode being in the form of a ring circumnavigating the shaft of the instrument such that the first portion of the second electrode acts as an active electrode when the instrument is operated to treat tissue disposed laterally of the longitudinal axis, and the second portion of the second electrode acts as a return electrode when the instrument is operated to treat tissue disposed in the longitudinal axis.

2. The electrosurgical instrument according to claim 1, wherein the first and second portions of the second electrode are integrally formed from a single metallic component.

3. The electrosurgical instrument according to claim 1, wherein the second electrode is set back axially with respect to the first electrode.

4. The electrosurgical instrument according to claim 1, wherein the first electrode is present on the extreme distal end of the instrument.

5. The electrosurgical instrument according to claim 1, wherein the third electrode is set back axially with respect to the first and second electrodes.

6. The electrosurgical instrument according to claim 1, wherein the third electrode is in the form of a metallic sheath provided on the instrument shaft.

7. The electrosurgical instrument according to claim 1, including a suction lumen extending along the length of the shaft.

8. The electrosurgical instrument according to claim 7, wherein the first tissue treatment electrode is provided with at least one aperture in communication with the suction lumen.

9. An electrosurgical system including a generator for generating radio frequency power, and an electrosurgical instrument, the generator comprising;
   (i) a radio frequency output stage having at least a pair of radio frequency output lines,
   (ii) a power supply coupled to the output stage for supplying power to the output stage, the power being sufficient to effect the electrosurgical vaporisation of tissue; and
   (iii) a controller capable of varying a radio frequency signal supplied to the radio frequency output lines;
   the electrosurgical instrument comprising an instrument shaft having a longitudinal axis, and an electrode assembly at one end of the shaft, the electrode assembly comprising first, second and third electrodes which are electrically insulated one from another by means of one or more insulation members, the first and second electrodes each having an exposed surface for treating tissue, the exposed surface of the first electrode being such as to treat tissue disposed in the longitudinal axis, and the exposed surface of the second electrode being such as to treat tissue disposed laterally of the longitudinal axis, and the second electrode comprising distinct first and second portions in electrical connection one with the other, the first portion of the second electrode being substantially planar and the second portion of the second electrode being in the form of a ring circumnavigating the shaft of the instrument, the system further including a switch means and a switching circuit operable in response to the switch means to vary the connections between the radio frequency output lines and the first, second and third electrodes such that, in a first condition, the first electrode is placed in circuit with the second portion of the second electrode such that, in use, a current path is established between the first and second electrodes so as to treat tissue adjacent the first electrode disposed on the longitudinal axis, and, in a second condition, the first portion of the second electrode is placed in circuit with the third electrode such that, in use, a current path is established between the second and third electrodes so as to treat tissue adjacent the second electrode disposed laterally of the longitudinal axis.

10. The electrosurgical system according to claim 9, wherein the switch means comprises a footswitch.

11. The electrosurgical system according to claim 9, wherein the switch means comprises a handswitch carried on the electrosurgical instrument.

12. The electrosurgical system according to claim 9, wherein the switching circuit is a part of the generator.

13. The electrosurgical system according to claim 9, wherein the switching circuit is a part of the electrosurgical instrument.

14. The electrosurgical system according to claim 9, wherein the generator and electrosurgical instrument are such that the instrument is designed to be operated in a conductive fluid, with the conductive fluid completing the current path between the electrodes.

15. The electrosurgical system according to claim 9, wherein the generator and electrosurgical instrument are such that the instrument is designed to be operated in a dry-field environment, with the electrodes being in direct contact with the tissue to be treated, and with the tissue completing the current path therebetween.

\* \* \* \* \*